United States Patent [19]

Bowen

[11] 4,376,096
[45] Mar. 8, 1983

[54] HEATING UNIT FOR DISINFECTING PURPOSES

[75] Inventor: John G. Bowen, Santa Ana, Calif.

[73] Assignee: Rincon Industries, Inc., Los Angeles, Calif.

[21] Appl. No.: 317,520

[22] Filed: Nov. 2, 1981

[51] Int. Cl.$^3$ .............................................. A61L 2/04
[52] U.S. Cl. .................................. 422/116; 219/441; 219/442; 422/119; 422/307; 422/38
[58] Field of Search ............... 422/38, 105, 300, 307, 422/116, 119; 219/523, 441, 442, 439

[56] References Cited

U.S. PATENT DOCUMENTS

| | | | |
|---|---|---|---|
| 1,293,964 | 2/1919 | Spink | 219/349 |
| 4,158,126 | 6/1979 | Seitz | 422/307 |
| 4,164,645 | 8/1979 | Dogliotti | 219/441 |
| 4,270,039 | 5/1981 | Hauser | 219/441 |
| 4,307,289 | 12/1981 | Thomas et al. | 422/300 |

*Primary Examiner*—Barry S. Richman
*Attorney, Agent, or Firm*—Keith D. Beecher

[57] ABSTRACT

An electrically energized heater is provided which has particular application as a dry disinfecting and sterilizing device for items such as soft lenses, dental handpieces, baby bottles, or the like, which cannot be placed in sterilizing solutions, and which cannot be subjected to excessive temperatures. The unit includes a housing, and a heat conductive substance such as wax, oil, or both, contained in the housing and used as a uniform heat transfer medium between electrical heating elements in the housing and the surface of a well which also is supported in the housing. The heater is generally applicable, and may be used to advantage, when it is desired to raise the temperature of an object or material to a particular disinfecting or sterilizing temperature for a given time period, and then to allow the temperature to cool down and return to ambient temperature condition, all without exceeding a critical temperature level, and without unnecessarily restricting the time period at which the particular disinfecting or sterilizing temperature is maintained. This is achieved in the heater of the invention by providing a manually resettable thermostatic switch immersed in the heat conductive substance which snaps off at the end of the given time period, and by also providing an automatic thermostatic switch immersed in the heat conductive substance and connected in series with the manual switch. The automatic thermostatic switch switches on and off during the given time period to hold the temperature below the critical level.

8 Claims, 8 Drawing Figures

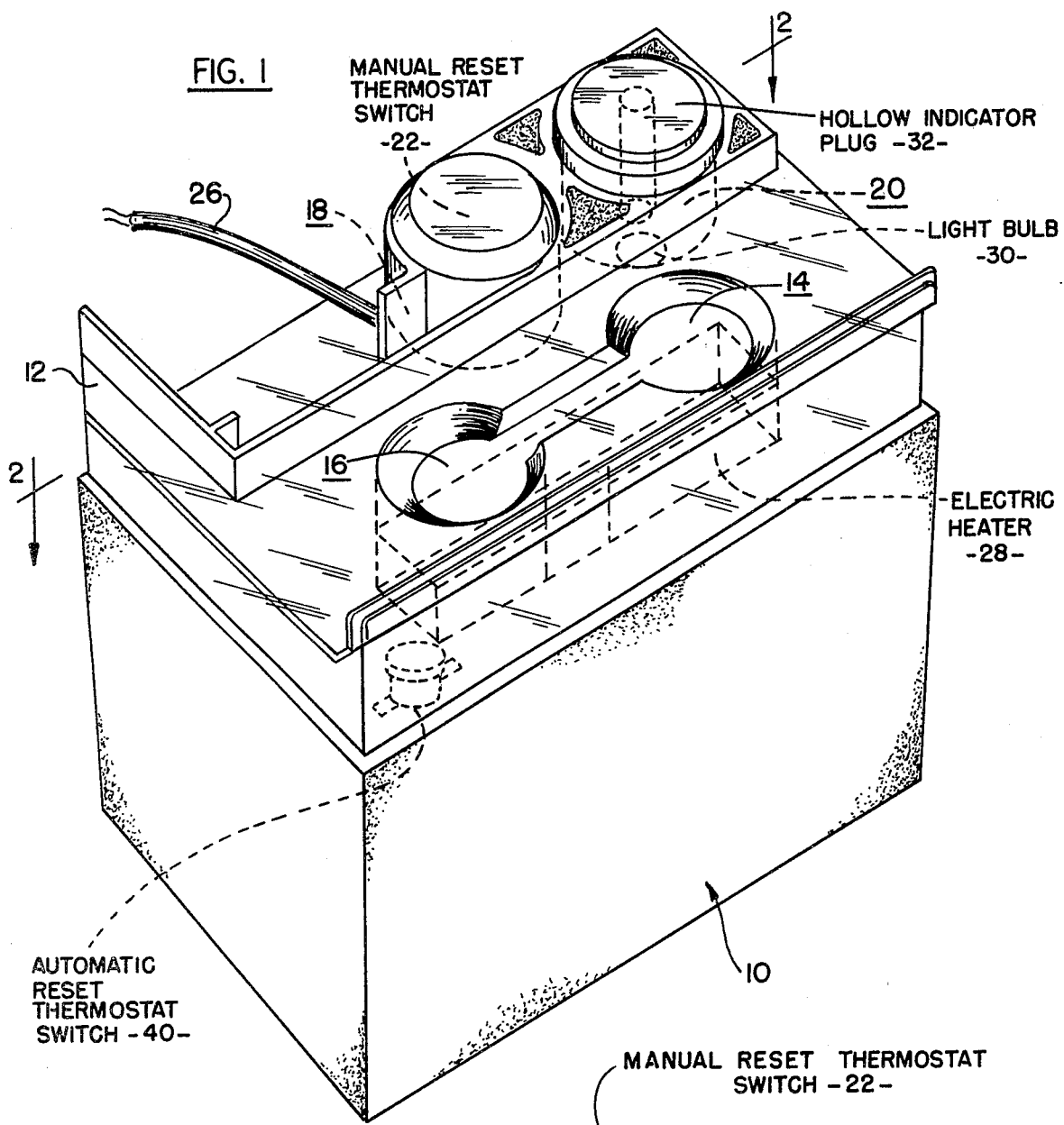
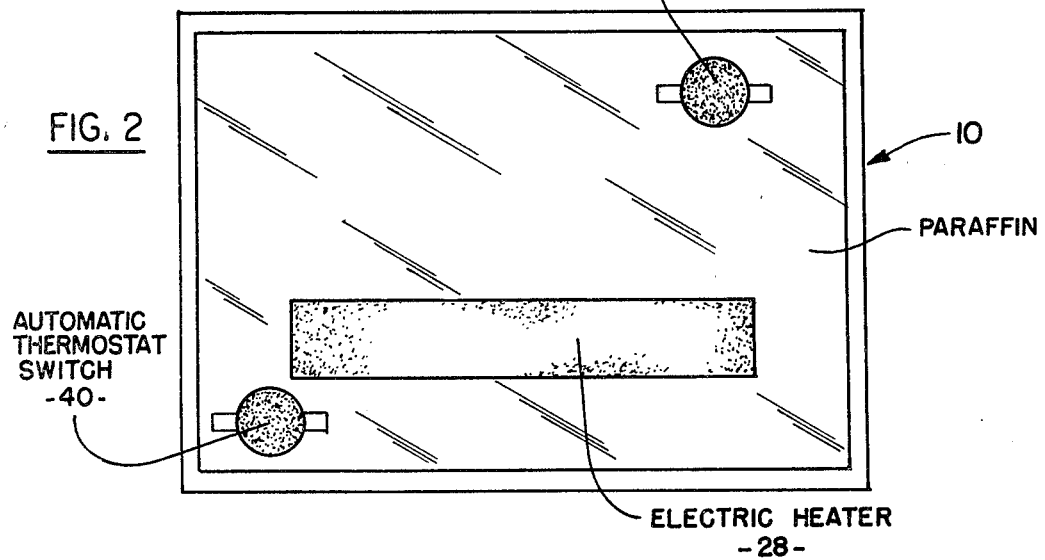

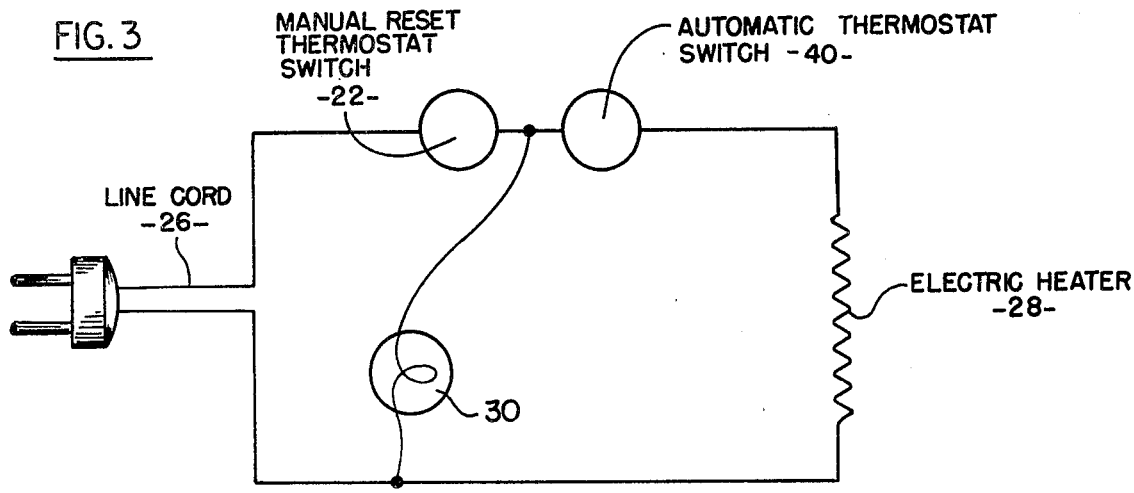
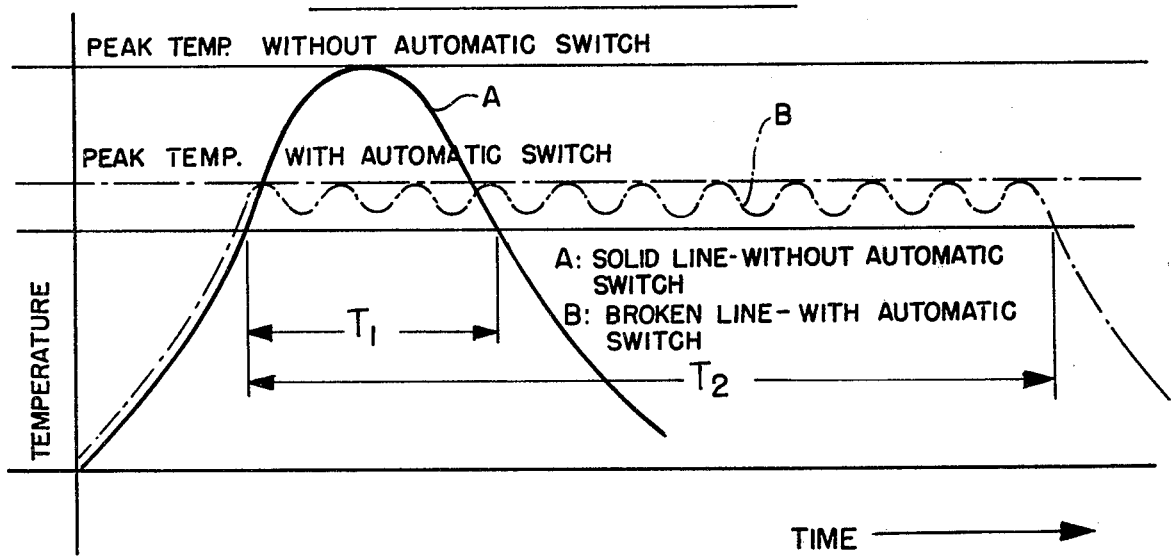

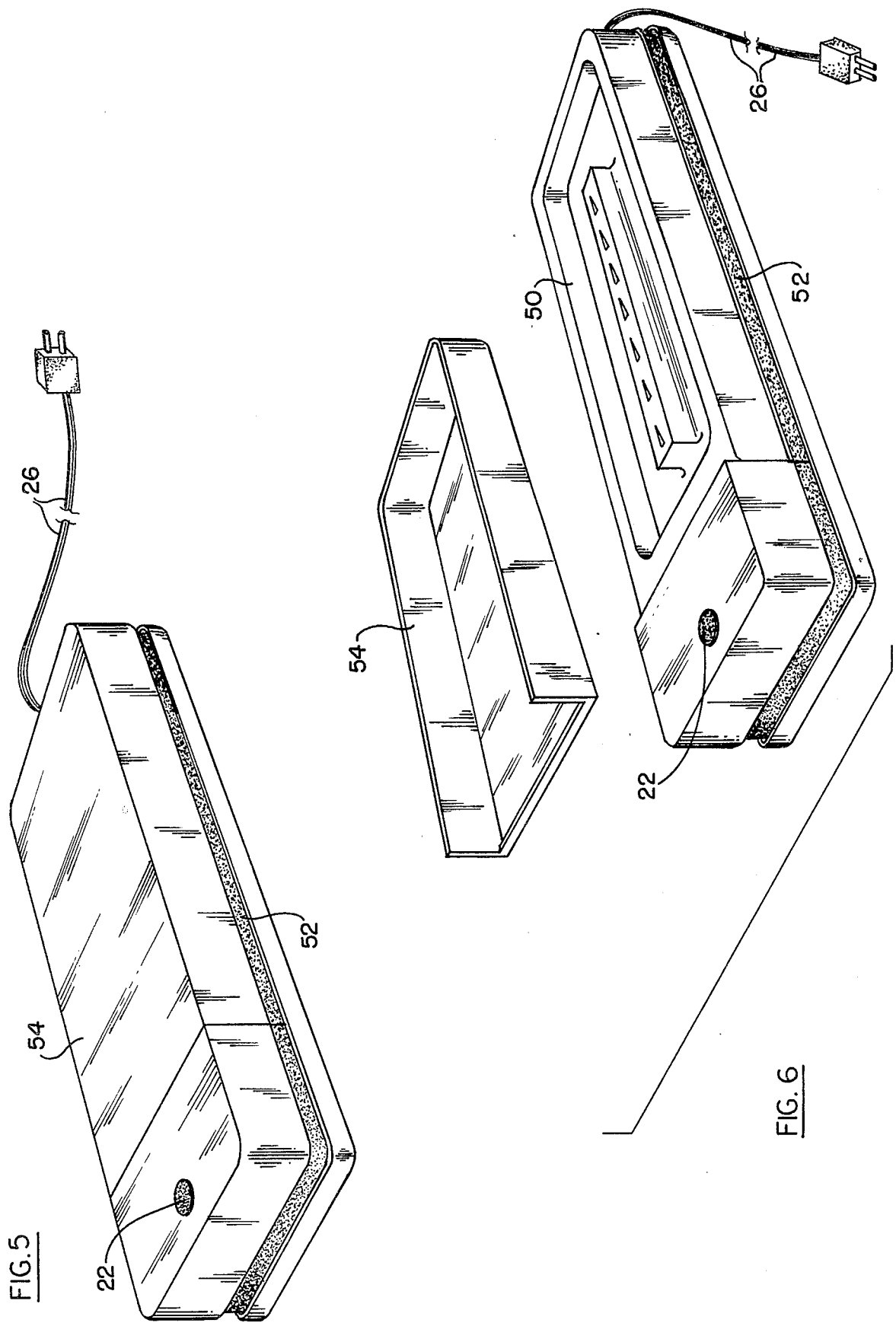

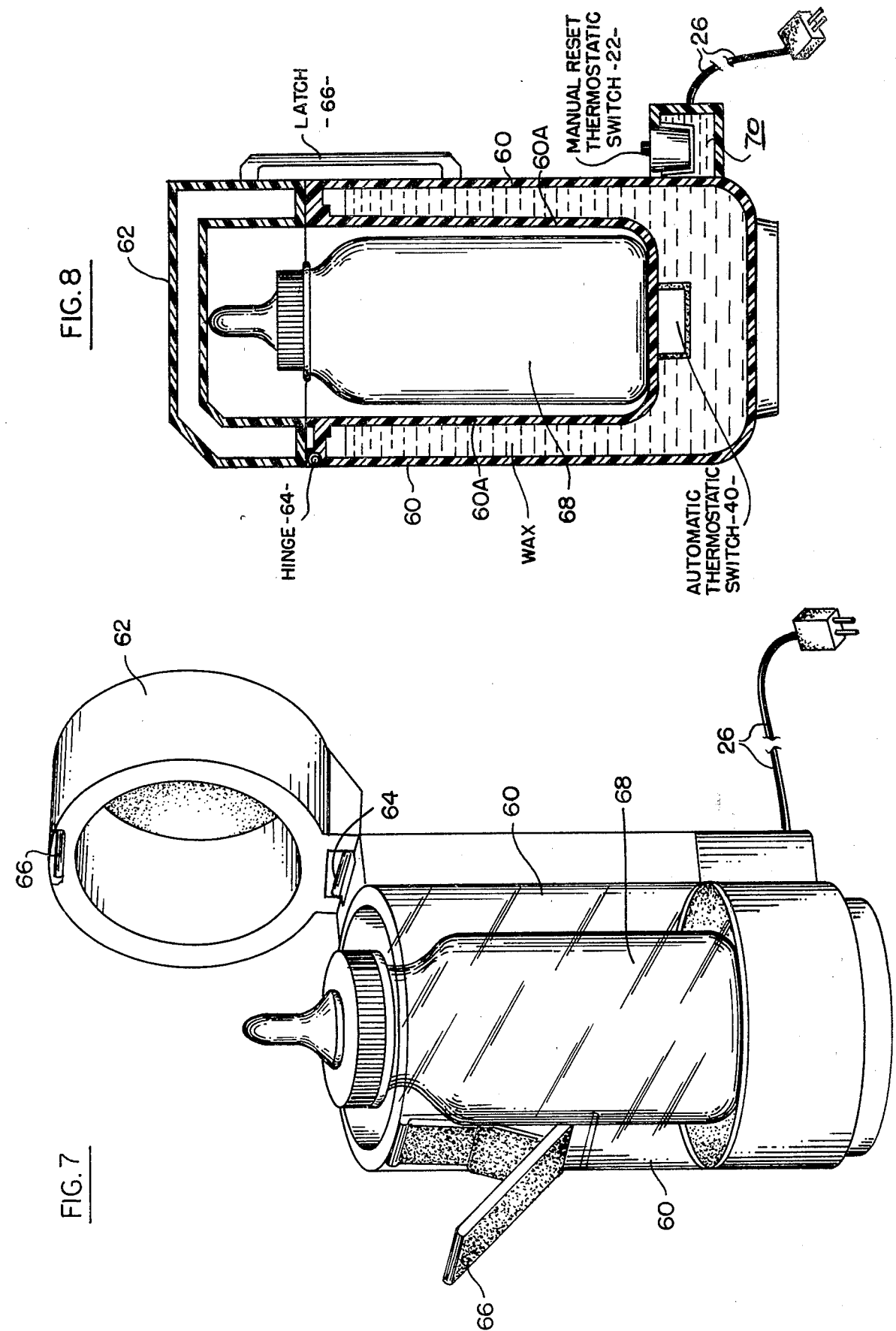

2

HEATING UNIT FOR DISINFECTING PURPOSES

BACKGROUND OF THE INVENTION

The heater of the invention is of the same general type described and claimed in U.S. Pat. No. 4,158,126 which is assigned to the present assignee, and which is used primarily to disinfect soft contact lenses. The heater of the present invention will also be described in conjunction with the disinfecting of soft contact lenses, as well as in conjunction with the disinfecting of dental handpieces and baby bottles although the heater has general applicability, as will become apparent as the description proceeds.

As pointed out in the patent, it is necessary to produce periodically an essentially disinfected condition in soft contact lenses so that bacterial organisms or their by-products will not cause harm to the wearer's eyes. Since the soft lens material is permeable to liquids, soaking the lenses in strong germicidal solution for disinfecting purposes will result in the lenses becoming impregnated with the solution, and this can lead to irritation to the user's eyes when the lenses are worn. In general, it has been found difficult to disinfect soft contact lenses by treatment with chemical or biochemical solutions which will not cause eye irritation to at least some percentage of the wearers.

As an alternate means for producing the desired disinfected condition in the soft contact lenses, and as also pointed out in the patent, heat may be used. The lenses must be kept immersed in psychologically normal saline solution, or its equivalent, when they are not being worn, to prevent the lens material from drying out. Therefore, for disinfecting the lenses they are first placed in a suitable container or lens holder, and a suitable amount of saline solution of proper concentration is added in sufficient quantities so that the lenses are totally immersed. The lense container is then closed and placed in a suitable heating unit for a given time period to disinfect the lenses.

The heating unit must raise the temperature of the saline solution and immersed lenses to the required temperature, and hold the lenses at or above this temperature for the required time, and then allow the lenses to cool back to ambient temperature. Typical values of the time and temperature deemed suitable for disinfecting the lenses require that the lenses be maintained at or above 80° C. for a period of ten minutes or more. Since aging of the lens material is accelerated by excessive temperatures and/or by extended time at elevated temperatures, it is desired that the heating unit be controlled so that excessive temperatures will not shorten the life of the lenses. This is achieved simply and economically in the heater of the present invention.

It is, accordingly, an objective of the present invention to provide an electrically energized heater which is capable of raising the temperature of an item to a desired elevated temperature, and for maintaining the temperature of the item at the elevated temperature for prolonged time periods, without any danger of a critical peak temperature being reached. This desired result is achieved in accordance with the invention by providing a heating unit which is economical in cost, and may be manufactured and sold at a relatively low price.

BRIEF DESCRIPTION OF THE DRAWINGS

FIG. 1 is a perspective representation of a heating unit which incorporates the teachings of the present invention and which is used to disinfect soft lenses;

FIG. 2 is a somewhat schematic view, taken along the line 2—2 of FIG. 1, and showing certain internal components of the heater of FIG. 1;

FIG. 3 is an electrical diagram illustrating the energizing circuit of the heating unit of FIGS. 1 and 2;

FIG. 4 are curves illustrating the manner in which the heating unit operates, as compared with the prior art type of unit;

FIGS. 5 and 6 are perspective views of the heating unit adapted to be used to disinfect dental handpieces, respectively with the cover on and off;

FIG. 7 is a perspective view of the unit adapted to be used to sterilize a baby bottle; and FIG. 8 is a side section of the unit of FIG. 7.

DETAILED DESCRIPTION OF THE ILLUSTRATED EMBODIMENT

The particular heating unit shown in FIG. 1 has the same configuration as the heating unit described in Copending Application Ser. No. 67,478 filed Aug. 17, 1979, and assigned to the present assignee, now U.S. Pat. No. 4,270,039 issued May 26, 1981.

The heating unit of FIG. 1 includes a bowl 10 which may be formed of any appropriate plastic material, such as high operating temperature grade polycarbonate. An incubator 12 is mounted on the top of and is sealed to the bowl 10, and it likewise may be formed of high temperature grade plastic, such as polycarbonate. The incubator extends down into the bowl. Both the bowl and incubator may be mounted in an appropriate housing, such as shown and described in U.S. Pat. No. 4,158,126.

The incubator 12 is formed to define two wells 14 and 16 of suitable dimensions to accept the maximum size lens case to be used as containers for the soft contact lenses during the heating/disinfecting operation of the unit, with the lenses being immersed in a saline solution in the lens case. It will be appreciated that different shapes and sizes of the wells may be provided depending upon the items to be disinfected by the unit. The incubator 12 is also shaped to define a switch cavity 18 and a wax fill hole 20. An appropriate pushbutton manually resettable thermostatic switch 22 is mounted in switch cavity 18. An electric cord 26 is connected through the switch 22, and an automatic reset thermostatic switch 40 to an electric heater 28 which is mounted on the underside of wells 14 and 16.

The bowl 10 is filled with wax, or other heat conductive material such as oil, through the fill hole 20. When the electric heater 28 is energized, the wax is heated to a molten state, during which the heat from the wax is transferred to the interior of the wells 14 and 16, as described in U.S. Pat. No. 4,158,126. An electric light bulb is embedded in the wax adjacent to the fill hole 20, and it is energized when the switch 22 is operated to indicate that the electric heater 28 is energized.

As described in the copending application Ser. No. 67,478, the fill hole 20 is closed by a hollow indicator plug 32. The indicator plug is also filled with wax, and it includes a transparent cover 32A. An indicator disc 34 is mounted on the bottom of the hollow plug 32, and it may be any appropriate color, such as red. A light pipe 36 extends through the hollow plug 32A and through indicator 34, so that light bulb 38 may be observed through the transparent cover 32A of the light plug when it is energized, so as to inform the user that the switch 22 has been operated to energize the electric heater 28.

When the wax, or other heat conductive medium, within the interior of bowl 10 reaches a molten state, the heat from that wax is transmitted to the interior of the hollow plug 32, so that the wax in the plug becomes molten, and when that occurs, the user can see the indicator disc 34 through the transparent cover 30A, and is thereby informed that the unit is in an operational state. This feature of the unit is covered in the Copending Application Ser. No. 67,478.

The wax, or other heat conductive medium, within bowl 10 acts as a heat transfer medium. When the unit is cold, and when it is energized by depressing the thermostatic switch 22 in cavity 18 through a resilient rubber diaphragm across the top of the cavity, the heating element 28 begins to heat up, as the circuit is completed, as shown in FIG. 3. This action causes the solid wax within the bowl adjacent to the heating element to melt, and the melted liquid wax begins to circulate by convection. The hot wax tends to rise carrying heat to the unmelted wax towards the top of the unit by convection currents, as well as to the walls of the lens holder wells 14 and 16. After substantially all of the wax within the bowl has been melted, no further heat input is required to supply heat of fusion in melting the wax, and the temperature of the liquid wax within the bowl will begin to rise above the melting temperature of the wax. When the molten wax reaches a predetermined temperature above its melting point, the thermostatic switch 22 in cavity 18 reaches its snapoff point. At that time, power is removed from the heating element 28, and the unit begins to cool down.

When the thermostatic switch 22 snaps off, it remains off until it is manually reset. In this way, a disinfecting cycle for the lenses in the saline solution in the lens case in wells 14 and 16 is initiated by actuating switch 22. When switch 22 is actuated to energize the heating element 28, light bulb 30 is energized, and can be observed through the indicator plug 32.

As shown by the solid curve A of FIG. 4, when the manual reset thermostatic switch 22 is used alone, the switch is closed at the beginning of a disinfecting cycle, and the temperature in the wells 14 and 16 rises to the desired temperature after a certain time has elapsed to permit the wax to become molten. Then, if the wells are to be maintained at or above the desired temperature for a certain time interval $T_1$, it is necessary for the temperature to rise above the desired temperature to a peak temperature at which the thermostatic switch 22 will snap off, after which the wax begins to cool down, as shown. However, in order to achieve a desired length of time in the disinfecting cycle at which the wells are at or above the desired disinfecting temperature, it is necessary for a peak temperature well above the desired temperature to be reached before the manual thermostat switch is permitted to snap off. Under many conditions, however, this peak temperature may be sufficiently high to create damage to the contact lenses, or other items being disinfected.

The use of the automatic thermostatic switch 40 in series with the manual thermostatic switch 22 permits long disinfecting periods to be achieved, such as designated $T_2$ without the temperature in the wells peaking to any substantial level above the desired temperature. This is shown by the broken curve B. When the thermostatic switch 22 is first closed, at the beginning of the disinfecting cycle, the curve rises to the desired temperature and then slightly above the desired temperature. However, when it rises slightly above the desired temperature the automatic thermostatic switch snaps off, causing the temperature to drop. However, when the temperature drops slightly, the automatic switch snaps on, and this continues until the temperature of the molten wax in the vicinity of the manual switch becomes high enough to cause the manual switch to snap off and thereby terminating the disinfecting cycle.

The embodiment of the invention shown in FIGS. 5 and 6 is intended particularly to be used for disinfecting dental handpieces. Present-day dental handpieces are usually air driven, and include a small turbine. The construction is such that the handpieces must be sterilized in a dry environment, and, because of the turbine bearings, the instrument cannot be heated over 130° C. However, the handpieces must be heated to a temperature above 100° C. to carry out the disinfection and the period of disinfection must be at least 20 minutes. In the embodiment of FIGS. 5 and 6, the handpiece may be heated to a temperature, for example, of 105° C.±4° C. in an unpressurized environment, and held at that temperature for 20 minutes, which is more than adequate to effect the disinfection of the instrument.

The embodiment of FIGS. 5 and 6 includes an elongated body section 50 in the form of an incubator which extends down into the interior of the unit. The interior of the unit includes the automatic thermostatic switch 40 and the manual thermostatic switch 22 of the previous embodiment, as well as appropriate electric heater elements, all connected in the manner shown in FIG. 3. The interior of the embodiment of FIGS. 5 and 6 is filled with paraffin wax, or other appropriate heat conductive material. The interior may be divided into compartments with a first compartment, containing the automatic thermostatic switch, being disposed under and surrounding the incubator 50, and with a second compartment surrounding the manual thermostatic switch 22. A transparent portion 52 extends around the unit, which is backed by an appropriate red strip adjacent each compartment within the unit. As in the previous embodiment, when the wax becomes molten in each compartment, the red indicator corresponding to that compartment can be viewed, to enable the user to be made aware of the fact that the unit is operating.

The paraffin wax in the compartment surrounding the manual thermostatic switch 22 may have a higher melting point than the paraffin in the compartment surrounding the incubator. The manual thermostatic switch can then be set to respond when the paraffin in the former compartment melts, so as to prolong the disinfecting time.

The unit of FIGS. 5 and 6 is provided with a cover 54 which fits over the body portion, but which does not form a pressure-tight joint with the body portion. The unit is energized by electric power through cord 26.

All that is necessary in order to disinfect the dental handpiece is to remove cover 54, and to lay one or two handpieces within the body 50. The cover 54 is then replaced, and the manual thermostatic switch 22 is operated to energize the unit. The automatic thermostatic switch within the interior of the unit assures that the handpieces within the unit will be disinfected at the desired temperature and for the desired length of time, at the end of which the thermostatic switch 22 will automatically switch off.

The embodiment of the invention shown in FIGS. 7 and 8 is a pressurized embodiment, and is intended primarily to sterilize a baby bottle, together with the nipple, and water contained in the bottle. The prime objective of the embodiment of FIGS. 7 and 8 is to provide a means, especially in localities where the water is not pure, whereby the baby bottle, nipple and water may be sterilized and disinfected, after which, appropriate formula can be mixed into the water, and the baby safely fed without fear of disease.

The embodiment of FIGS. 7 and 8 includes a body portion 60 which may be formed of appropriate transparent plastic material, and which has a re-entrant section 60A extending coaxially into the body 60 to form an incubator. The outer surface of the section 60A may be painted red, to be viewed through the transparent body portion when the wax, for example, contained within the body portion is heated and becomes transparent.

As in the embodiment of FIG. 1, the embodiment of FIGS. 7 and 8 includes manually reset thermostatic switch 22 and automatic thermostatic switch 40 immersed within the wax, the switches being connected in the manner shown in FIG. 3. However, the thermostatic switch 22 is placed in a separate compartment 70 which may contain paraffin having a higher melting point than the paraffin in the main compartment, so that the switch 22 will cut out at a precisely predetermined temperature corresponding to the melting temperature of the paraffin in compartment 70, so as to provide even greater sterilization time periods without exceeding a critical temperature level.

As before, in order to activate the unit, the thermostatic switch 22 is operated, and an electric heater (not shown) within the body 60 is energized to heat the wax, and cause the wax to become molten. The cap is loosely placed on the bottle, and as the incubator section is heated, the water vaporizes. A pressure-tight cover 62 is hinged to the body portion 60 by a hinge 64, and is securely latched by a latch 66. Then, as the water within the baby bottle vaporizes, pressure is built up within the interior of the unit. Pressure sterilization of the baby bottle, nipple and water occurs at a temperature of 115° C. and pressure of 15 psi, over an interval of 15 minutes. The circuitry of the embodiment of FIGS. 7 and 8 may be set to cause the internal temperature to rise to 124° C.±4° C. at 15 psi, and to hold that temperature for 15 minutes, so that full and complete sterilization is achieved. A pressure relief valve may be provided in cover 62 so that when the pressure within the unit reaches a certain level, the valve will pop open and vent any air in the unit to the atmosphere.

After that interval, the cover 62 may be opened, and, as stated, formula added to the water within the bottle. The heat retained by the wax will then hold the bottle at a feeding temperature of, for example, 40° C. for hours.

The invention provides, therefore, a simple and economical heating unit which is capable of providing relatively long sterilizing and disinfecting time periods at predetermined sterilizing temperatures, this being achieved without intermediate excessively high peak temperatures, which could cause damage to the items being disinfected.

It will be appreciated that while particular embodiments of the invention have been shown and described, modifications may be made, and it is intended in the claims to cover all modifications which come within the true spirit and scope of the invention.

What is claimed is:

1. An electrically energized heating unit for disinfecting soft lenses, dental hand pieces, baby bottles, and the like comprising: a bowl; an incubator supported on the bowl and containing at least one well extending into said bowl; electrically energized heating means mounted in said bowl; electric leads extending into said bowl for supplying electrical energy to said heating means; a heat conductive medium contained in said bowl to be heated by said heating means for conducting heat from said heating means to the outer surface of the well of said incubator so as to introduce heat into said well, said medium being a heat conductive wax to be heated from a solid state to a liquid state by said electrically energized heating means for conducting heat uniformly from said heating means to the outer surface of the well of said incubator; a manually resettable thermostatic switch connected to said leads and thermally coupled to the medium in said bowl; and an automatically resettable thermostatic switch connected in series with said manually resettable thermostatic switch and thermally coupled to said medium in said bowl, said automatically resettable thermostatic switch being imbedded in said wax adjacent to said electrically energized heating means, and said manually resettable thermostatic switch having a temperature set point higher than that of said automatic thermostatic switch and being imbedded in said wax at a point displaced a sufficient distance from said electrical heating means to permit said manually resettable thermostatic switch to act as a timer means to limit the time of energization of said heating means.

2. The combination defined in claim 1, in which said incubator is configured to receive a dental handpiece.

3. The combination defined in claim 1, in which said incubator is configured to receive a soft lens case.

4. The combination defined in claim 1, in which said incubator includes a pressure-tight cover to provide a pressurized environment within said incubator.

5. The combination defined in claim 4, in which said incubator is configured to receive a baby bottle.

6. The combination defined in claim 1, in which said bowl is divided into two compartments, and said automatically resettable thermostatic switch is positioned in a first of said compartments and said manually resettable thermostatic switch is positioned in a second of said compartments.

7. The combination defined in claim 6, in which said heat conductive medium in said first and second compartments is a heat conductive wax, with the wax in said second compartment having a higher melting point than the wax in said first compartment.

8. The combination defined in claim 7, and which includes indicating means for indicating when the wax in the second compartment reaches a liquid state and for indicating when the wax in said first compartment reaches a liquid state.

* * * * *